United States Patent [19]

Komatsu et al.

[11] 4,297,507

[45] Oct. 27, 1981

[54] PROCESS AND APPARATUS FOR PRODUCING TEREPHTHALIC ACID WITH HIGH PURITY

[75] Inventors: Makoto Komatsu; Yuji Takamizawa; Tazuo Ohta, all of Kurashiki, Japan

[73] Assignee: Mitsubishi Gas Chemical Co. Inc., Tokyo, Japan

[21] Appl. No.: 133,106

[22] Filed: Mar. 24, 1980

Related U.S. Application Data

[63] Continuation of Ser. No. 9,963, Feb. 6, 1979, abandoned.

[30] Foreign Application Priority Data

Feb. 20, 1978 [JP] Japan ................................. 53-17649

[51] Int. Cl.³ .............................................. C07C 51/16

[52] U.S. Cl. .................................................. 562/416
[58] Field of Search ................................ 562/421, 416

[56] References Cited

U.S. PATENT DOCUMENTS 3,012,038 12/1961 O'Neill et al. ..................... 562/421
3,708,531 1/1973 Croce et al. ....................... 562/421

*Primary Examiner*—Alan Siegel
*Attorney, Agent, or Firm*—Armstrong, Nikaido, Marmelstein & Kubovcik

[57] ABSTRACT

Terephthalic acid with a high purity for direct polymerization with glycols is produced by oxidizing p-tolualdehyde with a gas containing molecular oxygen in water as a solvent in the presence of bromine ions in an oxidation reactor using zirconium as a reactor material.

13 Claims, No Drawings

PROCESS AND APPARATUS FOR PRODUCING TEREPHTHALIC ACID WITH HIGH PURITY

This is a continuation, of application Ser. No. 9,963, filed Feb. 6, 1979 now abandoned.

This invention relates to a process and an apparatus for producing terephthalic acid with a high purity from p-tolualdehyde, and more particularly to a process and an apparatus for producing terephthalic acid of directly polymerizable grade from p-tolualdehyde in a reactor using zirconium as a reactor construction material.

Terephthalic acid is useful as a raw material for polyester, and since terephthalic acid with a low purity lowers the quality of the resulting polymers, terephthalic acid with a high purity is required. Especially in the production of polyester by direct polymerization, the purity of terephthalic acid must be extremely high. To produce terephthalic acid of directly polymerizable degree, a process for oxidizing p-xylene in a lower aliphatic carboxylic acid as a solvent using a catalyst of cobalt-manganese-bromine system was proposed (Japanese Patent Publication No. 25936/74) and has been widely employed in the industry.

The present inventors have made an extensive study of a process for producing terephthalic acid with a high purity for direct polymerization, using p-tolualdehyde as a raw material. The process for producing terephthalic acid from p-tolualdehyde has not been the study of extensive study so far, but processes for producing terephthalic acid by oxidizing an aromatic compound containing an alkyl substituent or a partially oxidized alkyl substituent in water as a solvent in the presence of bromine ions (Japanese Patent Publication No. 13921/64; British Patent Specification No. 833,438) and a process by oxidizing p-xylene and/or p-toluic acid in water containing hydrogen bromide (Japanese Laid-Open Patent Application No. 4019/71: U.S. Pat. No. 3,678,106) are known as closely relevant processes.

The present inventors conducted the oxidation reaction of p-tolualdehyde under the same conditions as those of said well known processes, and found that corrosion took place in a titanium reactor, and the purity of the resulting terephthalic acid was lowered.

The reactors so far employed for the production of terephthalic acid are usually made of titanium or stainless steel, and a stainless steel reactor is employed in the process of said Japanese Patent Publication No. 25936/74. Even in the present oxidation process, no corrosion takes place when a carboxylic acid is used as a solvent in place of water, but the solvent is burnt during the reaction, making an unpreferable loss.

The present inventors have studied materials of construction for the reactor applied to the process for producing terephthalic acid by oxidizing p-tolualdehyde in water as a solvent in the presence of bromine ions, and have found that no corrosion takes place in a zirconium reactor and terephthalic acid with a high purity can be obtained, and have established the present invention.

The present invention provides a process and an apparatus for producing terephthalic acid by oxidizing p-tolualdehyde with a gas containing molecular oxygen in water as a solvent in the presence of bromine ions, characterized by conducting the oxidation reaction in an oxidation reactor using zirconium as a material of construction.

The present invention will be described in detail below.

The reactor employed in the present invention is made of zirconium as a material of construction. It is not always necessary that the entire reactor is made of zirconium, but it is necessary that at least the inside wall of the reactor is lined or clad with a zirconium film or sheet thick enough to withstand a mechanical wear and a corrosion, for example, 0.5–6 mm, preferably 1–3 mm. The reactor material of construction can include not only zirconium, but also zirconium alloys containing a small amount of other metals, for example, zircaloy.

Hydrogen bromide, ethyl bromide, sodium bromide+hydrogen chloride, or any material capable of producing bromine ions under the reaction conditions can be used as the catalyst in the present invention. When compounds of heavy metals such as manganese, cerium, etc. are used together, terephthalic acid with a much higher purity can be obtained. The amount of bromine ions to be added is 0.5–12% by weight, preferably 0.5–6% by weight, more preferably 1–4% by weight, on the basis of the solvent. When the amount of bromine ions is less than 0.5% by weight on the basis of the solvent, p-tolualdehyde is considerably burnt and decomposed, and at the same time the contents of 4-carboxybenzaldehyde or coloring impurities are considerably increased in the resulting terephthalic acid. More than 12% by weight of the bromine ions suppresses the oxidation reaction.

Reaction temperature is 180°–280° C., preferably 210°–260° C. If the reaction temperature is below 180° C., the reaction intermediate, 4-carboxybenzaldehyde and coloring impurities are formed unpreferably in a large amount.

Reaction pressure is generally automatically determined by a process of keeping the reaction temperature at a certain value by evaporation and condensing and reflux operation of water as the solvent, but it is possible to keep the reaction temperature at a desired certain value by a heat exchange means from the outside. The pressure range is not particularly restricted, so long as it is in such a range as to keep the reactant in a liquid phase, but usually a pressure range of 10–50 kg/cm$^2$ gauge can be utilized.

Either oxygen or air can be used as an oxidizing agent, but it is economically advantageous to use air as the oxidizing agent.

It is satisfactory that the amount of water to be used as the solvent is at least twice the weight of the raw material p-tolualdehyde, and particularly preferable that it is 3–6 times the weight of p-tolualdehyde.

Reaction can be carried out by any of batchwise, semi-continuous and continuous operations.

In the present invention, no corrosion takes place at the reactor owing to the use of zirconium as a reactor material, and terephthalic acid with a high purity can be produced.

Zirconium is subject to more corrosion in an aqueous hydrobromic acid solution than titanium, for example, according to Corrosion Data Survey, page 101, published by National Association of Corrosion Engineers (1974), that is, a corrosion ratio of titanium is 0.05 mm or less/year in aqueous 10% and 20% hydrobromic acid solutions at 25° C., whereas that of zirconium is 1.27 mm or more/year in an aqueous 20% hydrobromic acid solution, and 0.5 mm or less/year in an aqueous 10% hydrobromic acid solution, both at 25° C. Thus, it is quite surprising and unexpected to find that zirconium is corroded less than titanium and can be advantageously utilized in the production of terephthalic acid with a high purity in the present invention.

Since water is used as the solvent in the present invention, no loss due to the combustion takes place during the reaction, and the resulting terephthalic acid as such can be used directly in polymerization with glycols without any purification.

The present invention will be described in detail, referring to Example.

EXAMPLE 671 g of water, 10.5 g of hydrogen bromide (1.5% by weight of hydrogen bromide) and 18.8 g of manganese bromide tetrahydrate were charged into a zirconium autoclave having a net capacity of 2 l, provided with a reflux cooler, a stirrer, a heater, a feed inlet, a gas inlet and a product outlet.

Nitrogen gas was introduced under pressure into the autoclave by the gas inlet to increase the pressure of the autoclave to 10 kg/cm$^2$ gauge, and then the autoclave was heated to 245° C. by the heater. After the autoclave was heated to 245° C., air was introduced into the autoclave by the gas inlet to replace the nitrogen with the air, and p-tolualdehyde was fed into the autoclave at a rate of 180 g/hr for one hour while blowing the air into the autoclave.

Even after the completion of feeding p-tolualdehyde, the air was continuously blown into the autoclave, and when the oxygen concentration of effluent gas was recovered to 21%, the air blowing was discontinued, and the resulting reaction product was taken out of the autoclave and separated into solid matter and a solution. The solid matter was washed with hot water.

4-carboxybenzaldehyde (4CBA) content and OD$_{340}$ value of the resulting terephthalic acid were measured. Then, the resulting terephthalic acid was directly reacted with ethylene glycol according to the well known method, and brightness (represented by L valve) of polymer chip of the resulting polyethylene terephthalate was measured. The results are given below:

4CBA: 332 ppm;
OD$_{340}$: 0.114;
Polymer L value: 75%;
Polymer color shade: colorless.

The term "OD$_{340}$" represents a light absorbancy determined by dissolving 2 g of terephthalic acid in 25 ml of 2 N KOH and measuring a light absorbancy of the resulting solution in a 50 mm cell at 340 mμ, and reflects the content of coloring impurities and coloring-inducing materials in terephthalic acid. The lower value means the presence of less coloring impurities and coloring-inducing materials.

"Polymer L value" of fine chips of polyethylene terephthalate resulting from the polymerization was measured by a colorimeter and represents a brightness of the polymer.

"Polymer color shade" is determined by visiually observing a degree of coloring of the polymer chips on the basis of the predetermined color shade of standard product, where the color shade is classified into five color groups in the order of increasing coloring degree, i.e. colorless, pale yellow, light yellow, yellow, and brownish yellow.

COMPARATIVE EXAMPLE

Oxidation reaction was carried out under the same conditions as in Example, except that a titanium autoclave was used in place of the zirconium autoclave.

The properties of the resulting terephthalic acid and the polymers derived therefrom are given below:

4CBA: 340 ppm;
OD$_{340}$: 0.125;
Polymer L value: 62%;
Polymer color shade: colorless (somewhat darkish).

Polyethylene terephthalate derived from terephthalic acid in Comparative Example had apparently a darkish color, and, thus, the terephthalic acid produced in the titanium reactor was judged to be not appropriate as terephthalic acid with a high purity for direct polymerization.

On the other hand, polyethylene terephthate derived from directly polymerizable terephthalic acid with a high purity industrially obtained by oxidation of p-xylene in acetic acid as a solvent in the presence of a catalyst including hydrogen bromide in a titanium reactor had a brightness of 75% in L value and a color shade "colorless", which was equivalent to that obtained in the zirconium reactor in the foregoing Example.

What is claimed is:

1. A process for producing terephthalic acid of high purity suitable for direct polymerization by oxidizing p-tolualdehyde at 180°–280° C. with a gas containing molecular oxygen in a solvent consisting of water in the presence of bromine ions, the concentration of the bromine ions being 0.5–12% by weight on the basis of the solvent, in a reactor using zirconium or a zirconium alloy as a reactor material.

2. A process according to claim 1, wherein the oxidation reaction is conducted in the presence of 0.5–6% by weight of the bromine ions on the basis of the solvent.

3. A process according to claim 2, wherein the oxidation reaction is conducted in the presence of 1–4% by weight of the bromine ions on the basis of the solvent.

4. A process according to claim 1, wherein the oxidation reaction is conducted at 210°–260° C.

5. A process according to claim 1, wherein the oxidation reaction is carried out under a pressure of 10–50 kg/cm$^2$ gauge.

6. A process according to claim 1, wherein the oxidation reaction is conducted with air.

7. A process according to claim 1, wherein the oxidation reaction is conducted in the water in an amount of at least twice the weight of p-tolualdehyde.

8. A process according to claim 7, wherein the amount of water is 3–6 times the weight of p-tolualdehyde.

9. A process according to claim 1, wherein the oxidation reaction is conducted batchwise, semi-continuously or continuously.

10. In a process for producing terephthalic acid by oxidizing p-tolualdehyde in a liquid phase with a gas containing molecular oxygen in the presence of bromine ions at an elevated temperature and under a pressure of 10–50 kg/cm$^2$ gauge, the improvement comprising conducting the oxidation in water as solvent at 180°–280° C. in a reactor having a zirconium or zirconium alloy inner surface.

11. The process of claim 1 in which the p-tolualdehyde is oxidized in the presence of compounds of heavy metals selected from the group consisting of manganese and cerium.

12. The process of claim 10 in which the reactor has a zirconium or zirconium alloy lining and said lining is 0.5–6 mm thick.

13. The process of any one of claims 1 or 10 in which the zirconium alloy is zircaloy.

* * * * *